(12) United States Patent
Spence et al.

(10) Patent No.: US 10,549,020 B2
(45) Date of Patent: Feb. 4, 2020

(54) COUNTERPULSATION DEVICE DRIVER APPARATUS, METHOD AND SYSTEM

(71) Applicant: Abiomed, Inc., Drive, MA (US)

(72) Inventors: Paul Spence, Louisville, KY (US); Rob Dowling, Louisville, KY (US); Robert T. V. Kung, Andover, MA (US); Thorsten Siess, Wuerselen (DE); Eric Gratz, Louisville, KY (US); Gerd Spanier, Aachen (DE)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 15/923,734

(22) Filed: Mar. 16, 2018

(65) Prior Publication Data

US 2018/0207337 A1     Jul. 26, 2018

Related U.S. Application Data

(63) Continuation of application No. 15/398,833, filed on Jan. 5, 2017, now Pat. No. 9,950,102, which is a
(Continued)

(51) Int. Cl.
*A61M 1/10* (2006.01)
*A61M 1/12* (2006.01)
(Continued)

(52) U.S. Cl.
CPC ............ *A61M 1/1086* (2013.01); *A61M 1/10* (2013.01); *A61M 1/106* (2013.01); *A61M 1/107* (2013.01);
(Continued)

(58) Field of Classification Search
CPC .. A61M 1/1086; A61M 1/106; A61M 1/1044; A61M 1/107; A61M 1/122;
(Continued)

(56) References Cited

U.S. PATENT DOCUMENTS 7,572,217 B1    8/2009  Koenig et al.
7,892,162 B1    2/2011  Jeevanandam et al.
(Continued)

FOREIGN PATENT DOCUMENTS

CA    2778450 A1    4/2011
WO    1999016481 A1    4/1999

OTHER PUBLICATIONS

PCT International Search Report for International Serial No. PCT/US12/66367, dated Jan. 31, 2013 (4 pages).
(Continued)

*Primary Examiner* — Amanda K Hulbert
*Assistant Examiner* — Natasha Patel
(74) *Attorney, Agent, or Firm* — White & Case LLP

(57) ABSTRACT

A method of operating a counterpulsation device (CPD) in a human or animal subject is disclosed, the method including: receiving a heart beat signal indicative of the heart beat of the subject; providing counterpulsation therapy by controlling the pressure supplied to a CPD drive line in pneumatic communication with the CPD to cause the CPD to alternately fill with blood and eject blood with a timing that is determined at least in part based on the heart beat signal; while providing counterpulsation therapy, receiving a CPD drive line pressure signal indicative of the pressure in the CPD drive line; and adjusting the pressure supplied to the drive line based at least in part on the drive line pressure signal.

20 Claims, 11 Drawing Sheets

Related U.S. Application Data continuation of application No. 14/360,474, filed as application No. PCT/US2012/066367 on Nov. 21, 2012, now Pat. No. 9,566,374.

(60) Provisional application No. 61/563,238, filed on Nov. 23, 2011.

(51) Int. Cl.
*A61B 17/062* (2006.01)
*A61B 17/11* (2006.01)

(52) U.S. Cl.
CPC ........ A61M 1/1008 (2014.02); A61M 1/1044 (2014.02); A61M 1/122 (2014.02); *A61B 17/062* (2013.01); *A61B 2017/1107* (2013.01); *A61B 2017/1135* (2013.01); *A61M 1/1037* (2013.01); *A61M 1/1062* (2014.02); *A61M 1/12* (2013.01); *A61M 2205/3337* (2013.01); *A61M 2205/502* (2013.01); *A61M 2230/06* (2013.01)

(58) Field of Classification Search
CPC .... A61M 1/1008; A61M 1/10; A61M 1/1062; A61M 1/12; A61M 2205/3337; A61M 2205/502; A61M 2230/06; A61M 1/1037; A61B 17/062; A61B 2017/1135; A61B 2017/1107
See application file for complete search history.

(56) References Cited

U.S. PATENT DOCUMENTS

| | | | |
|---|---|---|---|
| 7,914,436 B1* | 3/2011 | Kung | A61M 1/106 600/18 |
| 2002/0147495 A1 | 10/2002 | Petroff | |
| 2003/0074144 A1* | 4/2003 | Freed | A61M 1/1072 702/50 |
| 2004/0167376 A1* | 8/2004 | Peters | A61M 1/1037 600/18 |
| 2005/0096496 A1 | 5/2005 | Spence | |
| 2006/0167334 A1 | 7/2006 | Anstadt et al. | |
| 2006/0236756 A1 | 10/2006 | Rinaldi et al. | |
| 2008/0275520 A1 | 11/2008 | Hopper et al. | |
| 2008/0306329 A1 | 12/2008 | Lu et al. | |
| 2009/0318983 A1 | 12/2009 | Armoundas et al. | |
| 2010/0268333 A1* | 10/2010 | Gohean | A61M 1/1081 623/3.14 |
| 2010/0274308 A1 | 10/2010 | Scott | |
| 2010/0280306 A1 | 11/2010 | Spence | |
| 2011/0196189 A1* | 8/2011 | Milbocker | A61M 1/106 600/16 |
| 2014/0371519 A1 | 12/2014 | Spence et al. | |

OTHER PUBLICATIONS

Supplementary Search Report for European Patent Application No. 12851437.9, dated Nov. 11, 2015 (15 pages).

* cited by examiner

COUNTERPULSATION DEVICE DRIVER APPARATUS, METHOD AND SYSTEM

CROSS REFERENCE TO RELATION APPLICATIONS

This application is a continuation of U.S. patent application Ser. No. 15/398,833, filed Jan. 5, 2017 (allowed), which is a continuation of U.S. patent application Ser. No. 14/360,474, filed May 23, 2014 (now U.S. Pat. No. 9,566,374), which is a national stage of International Application No. PCT/US2012/066367, filed Nov. 21, 2012 (published), which claims the benefit of U.S. provisional Application No. 61/563,238, filed Nov. 23, 2911, entitled COUNTERPULSATION DEVICES, SYSTEMS, AND METHODS, the entire contents of which are incorporated herein by reference. This application is also related to International Patent Application No. PT/US12/66292 filed Nov. 21, 2012 entitles GRAFT FOR USE WITH COUNTERPULSATION DEVICE, the entire contents of which are incorporated herein by reference.

BACKGROUND

The following section is presented for informational purposes only. The inclusion of material in this section should not be considered to be an admission that such material is prior art to the present application.

Cardiac disorders such as congestive heart failure affect more than five million subjects in the United States alone. Many subjects suffering from such disorders require mechanical circulatory support. Counterpulsation therapy maybe used for the treatment of cardiac disorders. Counterpulsation is a technique that synchronizes the external pumping of blood with the heart's cycle to assist the circulation and decreasing the work of the heart. Counterpulsation pumps eject when the heart is filling (relaxation period) to increase blood flow and oxygen to the heart. Counterpulsation pumps fill when the heart is ejecting to decrease the hearts workload and lessen oxygen demand.

Counterpulsation may be implemented using an implanted pump device, referred to as a counterpulsation device (CPD). The pumping action of the CPD may be synched to the subject's heartbeat to provide counterpulsation, e.g. using a detected EKG signal.

SUMMARY

The applicants have developed devices, systems, and methods as described herein for use with counterpulsation devices (CPDs).

In one aspect, a method of operating a counterpulsation device (CPD) in a human or animal subject is disclosed, the method including: receiving a heart beat signal indicative of the heart beat of the subject; providing counterpulsation therapy by controlling the pressure supplied to a CPD drive line in pneumatic communication with the CPD to cause the CPD to alternately fill with blood and eject blood with a timing that is determined at least in part based on the heart beat signal; while providing counterpulsation therapy, receiving a CPD drive line pressure signal indicative of the pressure in the CPD drive line; and adjusting the pressure supplied to the drive line based at least in part in the drive line pressure signal.

In some embodiments, adjusting the pressure within the drive line based at least in part on the drive line pressure signal includes analyzing the drive line pressure signal to determine a full fill or full empty condition of the CPD.

In some embodiments, analyzing the drive pressure signal to determine a full fill or full empty condition of the CPD includes analyzing the change in drive line pressure as a function of time.

In some embodiments, the CPD includes drive chamber in pneumatic communication with the drive line and a blood chamber that is sealed from the drive chamber by a membrane. In some embodiments, analyzing the drive line pressure signal to determine a full fill or full empty condition of the CPD includes detecting a feature in the drive line pressure signal indicative of the membrane reaching a substantially stationary end position.

Some embodiments include detecting the temporal location of the full fill or full empty condition during an operation cycle of the CPD, comparing the temporal location to a desired range; and if the temporal location is outside of the desired range, adjusting the pressure supplied to the drive line.

Some embodiments include, during emptying of the CPD: determining if the temporal location of the full empty condition occurs at a time earlier than the desired range and, if so, adjusting the drive line pressure to slow the emptying.

Some embodiments include, determining if the temporal location of the full empty condition occurs at a time later than the desired range or does not occur and, if so, adjusting the drive line pressure to speed up the emptying.

Some embodiments include, during filling of the CPD: determining if the temporal location of the full fill condition occurs at a time earlier than the desired range and, if so, adjusting the drive line pressure to slow the filling.

Some embodiments include, during filling of the CPD: determining if the temporal location of the full fill condition occurs at a time later than the desired range or does not occur and, if so, adjusting the drive line pressure to speed up the filling.

In some embodiments, adjusting the pressure supplied to the drive line includes adjusting one or more operating parameters of a pump device pneumatically coupled to the CPD drive line.

In some embodiments, the pump device includes a compressor, and adjusting one or more operating parameters of the pump device includes adjusting an operating parameter of the compressor.

In some embodiments, the pump device includes one or more pressure or vacuum chambers. In some embodiments, adjusting one or more operating parameters of the pump device includes controlling one or more venting valves associated with the one or more pressure or vacuum chambers.

In some embodiments, the heart beat signal includes an EKG signal.

Some embodiments include controlling the drive line pressure based at least in part on the heartbeat signal to cause the CPD to eject blood when the heart is filling and to fill with blood when the heart is ejecting blood.

In another aspect, an apparatus for controlling the operation of a counterpulsation device (CPD) in a human or animal subject is disclosed, the apparatus including a controller configured to: receive a heart beat signal indicative of the heart beat of the subject; provide counterpulsation therapy by controlling the pressure supplied to a CPD drive line in pneumatic communication with the CPD to cause the CPD to alternately fill with blood and eject blood with a timing that is determined at least in part based on the heart beat signal; while providing counterpulsation therapy, receive a CPD drive line pressure signal indicative of the pressure in the CPD drive line; and adjust the pressure supplied to the drive line based at least in part on the drive line pressure signal.

In some embodiments, the controller is configured to adjust the pressure within the drive line based at least in part on the drive line pressure signal by analyzing the drive line pressure signal to determine a full fill or full empty condition of the CPD.

In some embodiments, the controller is configured to analyze the drive line pressure signal to determine a full fill or full empty condition of the CPD by analyzing the change in drive line pressure as a function of time.

In some embodiments, the CPD includes drive chamber in pneumatic communication with the drive line and a blood chamber that is sealed from the drive chamber by a membrane. In some embodiments, the controller is configured to analyze the drive line pressure signal to determine a full fill or full empty condition of the CPD by detecting a feature in the drive line pressure signal indicative of the membrane reaching a substantially stationary end position.

In some embodiments, the controller is configured to: detect the temporal location of the full fill or full empty condition during an operation cycle to the CPD, compare the temporal location to a desired range; and if the temporal location is outside of the desired range, adjust the pressure supplied to the drive line.

In some embodiments, the controller is configured to, during emptying of the CPD: determine if the temporal location of the full empty condition occurs at a time earlier than the desired range and, if so, adjust the drive line pressure to slow the emptying.

In some embodiments, the controller is configured to, during emptying of the CPD: determine if the temporal location of the full empty condition occurs at a time later than the desired range or does not occur and, if so, adjust the drive line pressure to speed up the emptying.

In some embodiments, the controller is configured to, during filling of the CPD: determine if the temporal location of the full fill condition occurs at a time earlier than the desired range and, if so, adjust the drive line pressure to slow the filling.

In some embodiments, the controller is configured to, during filling of the CPD: determine if the temporal location of the full fill condition occurs at a time later than the desired range or does not occur and, if so, adjust the drive line pressure to speed up the filling.

In some embodiments, the controller is configured to adjust the pressure supplied to the drive line by adjusting one or more operating parameters of a pump device pneumatically coupled to the CPD drive line.

In some embodiments, the pump device includes a compressor. In some embodiments, adjusting one or more operating parameters of the pump device includes adjusting an operating parameter of the compressor.

In some embodiments, the pump device includes one or more pressure or vacuum chambers, and where adjusting one or more operating parameters of the pump device includes controlling one or more venting valves associated with the one or more pressure or vacuum chambers.

In some embodiments, the heart beat signal includes an EKG signal.

In some embodiments, the controller is configured to control the drive line pressure based at least in part on the heartbeat signal to cause the CPD to eject blood when the heart is filling and to fill with blood when the heart is ejecting blood.

Some embodiments include the pump device.

Some embodiments include a sensor configured to generate the drive line pressure signal.

In another aspect, a system is disclosed including: a CPD; and the apparatus of any one of the types described above, operatively coupled to the CPD. Some embodiments include the CPD drive line. Some embodiments include a sensor configured to generate the heart beat signal. In some embodiments, the sensor configured to generate the heart beat signal includes an EKG unit. Some embodiments include a graft configured to connect the CPD to a blood vessel in the subject.

Various embodiments may include any of the elements described above, alone or in any suitable combination.

BRIEF DESCRIPTION OF DRAWINGS

The accompanying drawings are presented for illustrative purposes only and are not intended to be drawn to scale.

DETAILED DESCRIPTION

The following disclosure describes a graft and related methods for use with an implantable counterpulsation device (CPD).

Figure 1:
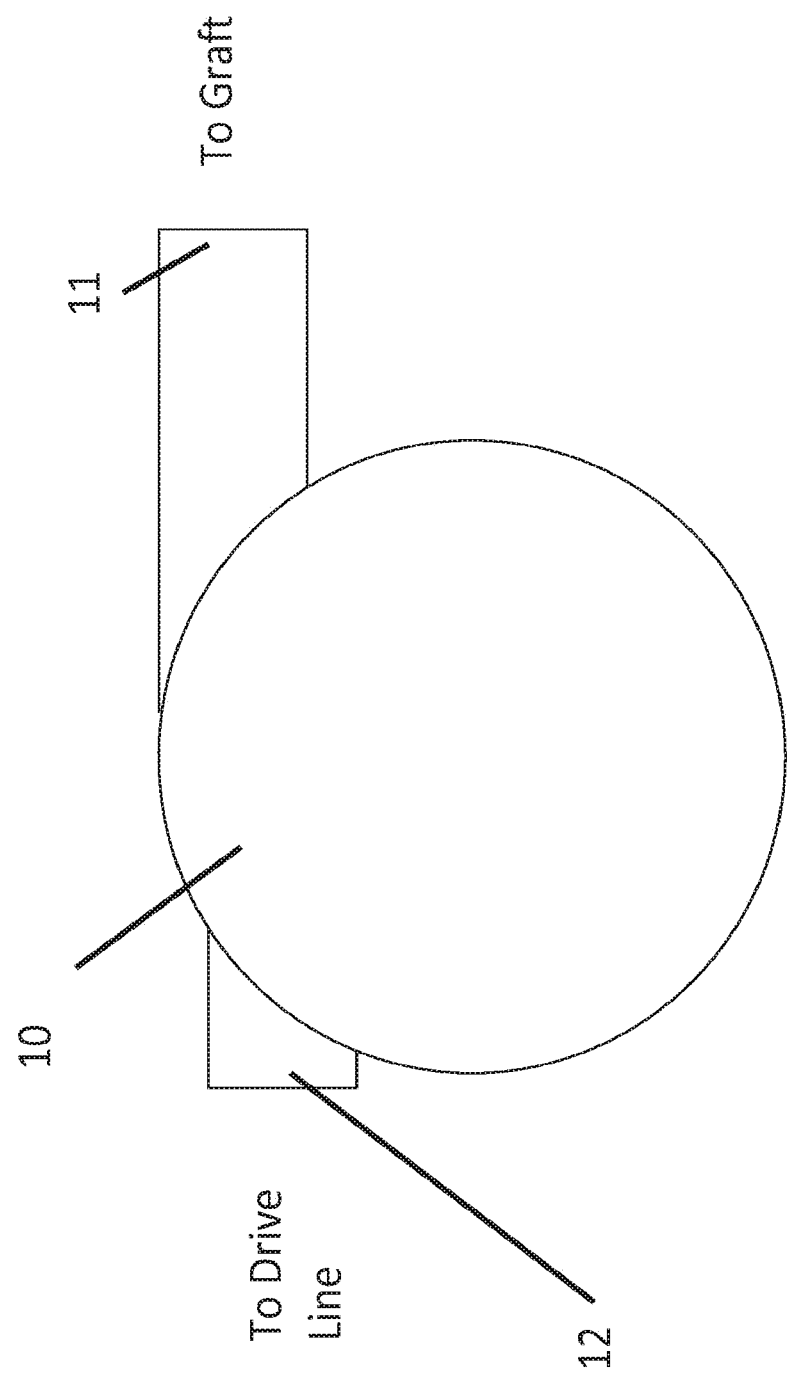
FIG. 1 is an illustration of a counterpulsation device (CPD).

FIG. 1 shows an exemplary embodiment of a CPD 10. The CPD 10 has a pump port 11 that can be attached to blood vessel of a subject using a graft 100 (not shown, described below). The pump port 11 allows for inflow and outflow of blood from the CPD 10. The CPD 10 also includes a drive line port 12, that can receive a drive line 201 (not shown, described below) that may control the operation of the CPD 10, e.g., as described below. In some embodiments, the CPD 10 may include a blood pump, e.g., a valveless pump, in fluid communication with the pump port 11. In some embodiments, the CPD includes a blood chamber that is separated from a drive chamber be a membrane. The drive chambers is in pneumatic communication with the drive line, while the blood chamber is in fluid communication with the blood vessel via the graft 100.

In some embodiments, the CPD 10 may be of the type available under the Symphony® product line available from Abiomed, Inc., of Danvers, Mass.

Figure 2:
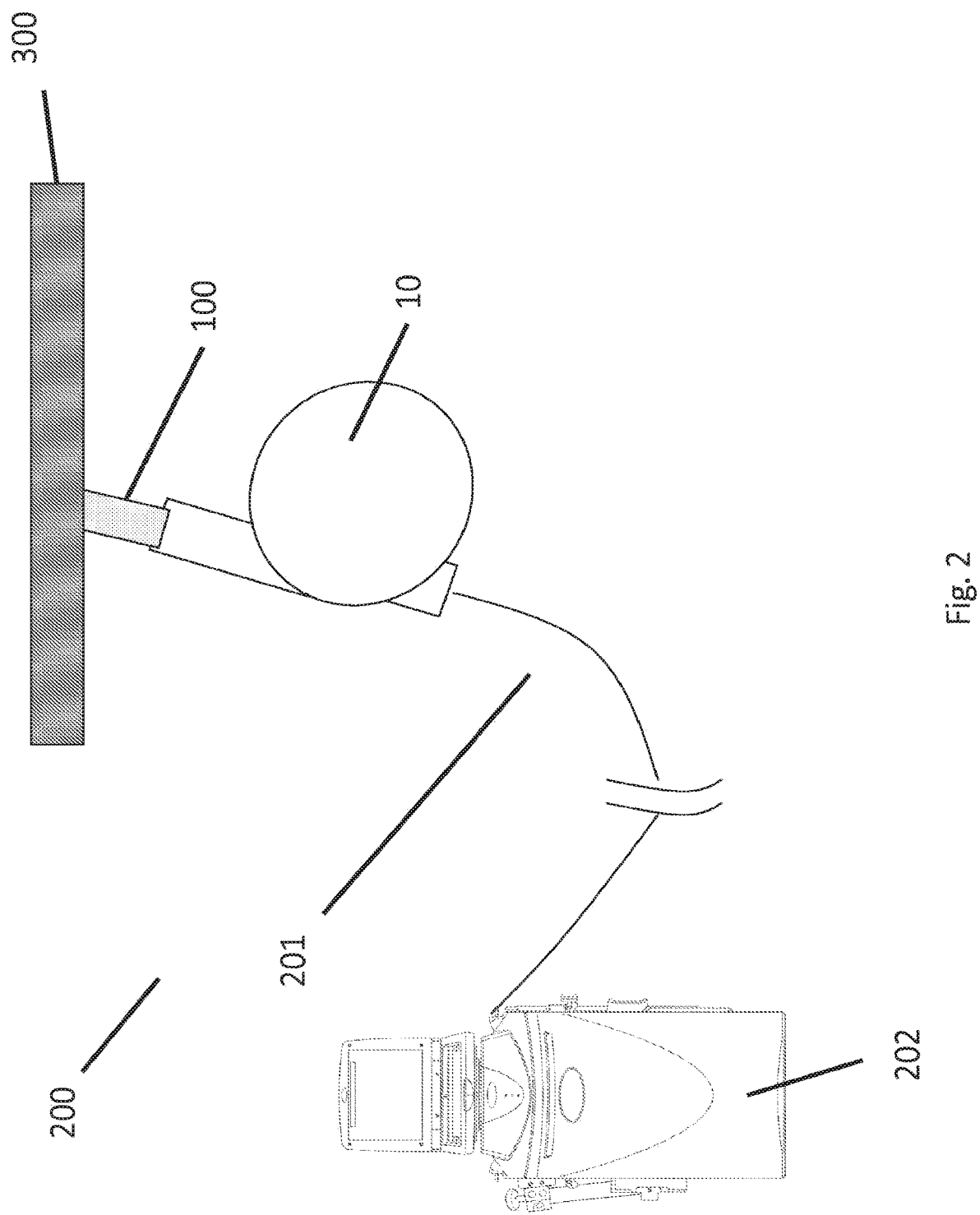
FIG. 2 is an illustration of a CPD system including a CPD, CPD driver, and CPD graft.

FIG. 2 shows an exemplary CPD system 200 used to provide counterpulsation therapy to a subject. The CPD 10 is attached to a blood vessel 300 (e.g., the subclavian artery) using a graft 100, e.g., of the type described below. In some embodiments, the CPD may be implanted in the subject, e.g., superficially in a so called "pacemaker pocket" outside of the chest cavity of the subject, with the graft 100 providing fluid communication between the CPD and the blood vessel 300 within the chest cavity.

A drive line 201 (e.g., a pneumatic line) attaches the CPD 10 to a drive controller 202, to allow for control of the operation of the CPD 10. For example, in some embodiments, the drive controller 202 synchronizes the external pumping of blood from the CPD 10 with the subject's heart's cycle to assist the circulation and decrease the work of the heart. The controller may cause the CPD 10 to eject blood when the heart is relaxing to increase blood flow and oxygen to the heart, and to fill the pump passively or actively when the heart is contracting to eject blood to decrease the heart's workload and lessen oxygen demand. For example the drive controller 202 may alternately apply positive pressure and vacuum through the drive line 201 to empty and fill the CPD 10. The pumping action of the CPD 10 may be synched to the subject's heartbeat to provide counterpulsation, e.g., using a detected EKG signal sent to the drive controller 202.

Figure 3:
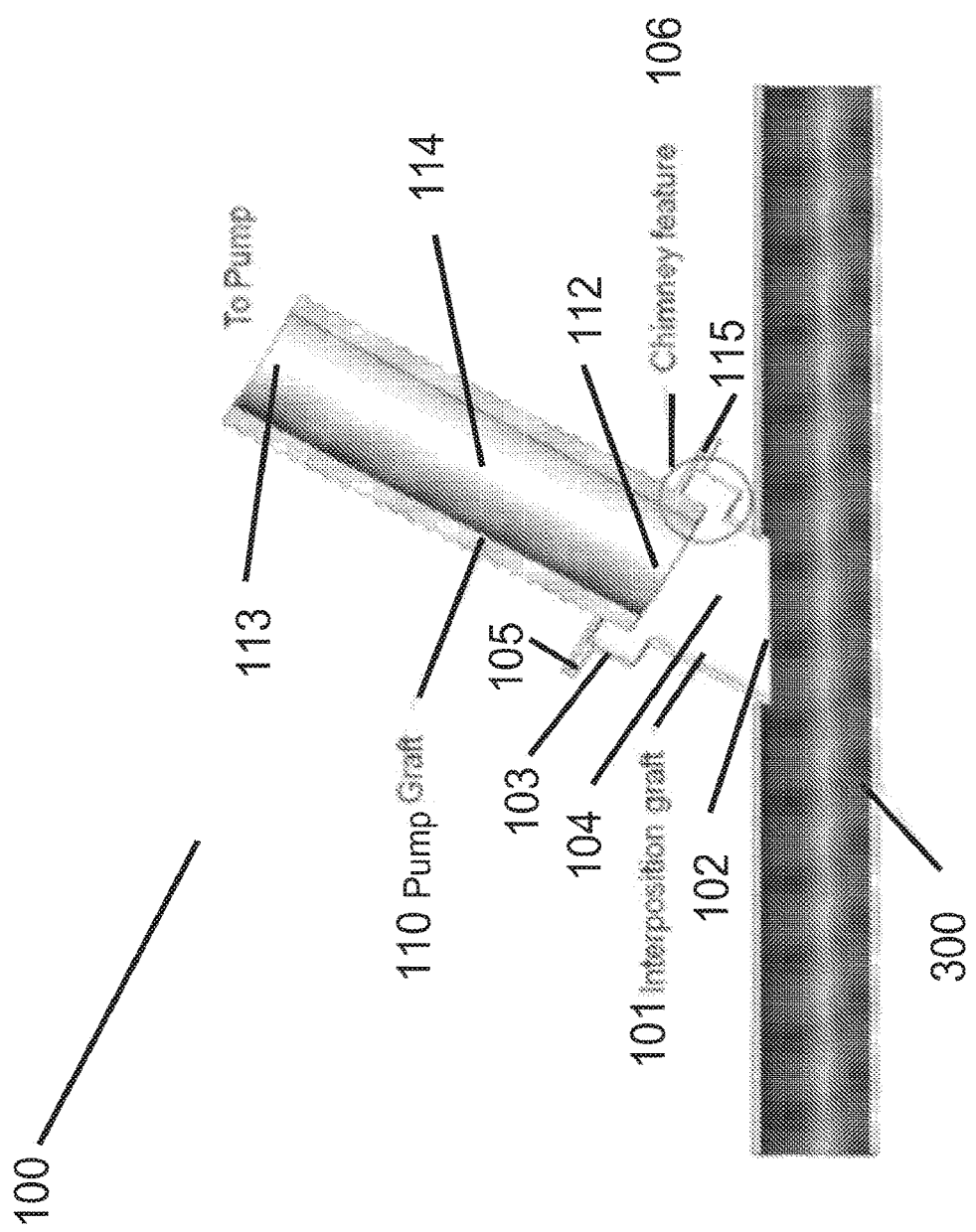
FIG. 3 shows a detailed view of an embodiment a CPD graft.

FIG. 3 shows a detailed view of an embodiment the graft 100. The graft 100 is made up of a interposition graft 101 and a pump graft 110. The interposition graft 101 has a first end 102 attached using any suitable anastomosis technique to the blood vessel 300 and a second end 103 attached to the pump graft 110. For example, in some embodiments, the interposition graft 101 is sewn to the vessel 300. An interior passage 104 (e.g. a tubular passage) is formed in the interposition graft 101 that provides fluid communication with the pump graft 110.

In some embodiments, the graft 100 may include one or more of the connectors described in U.S. Pat. Pub. No. 2012/0209057 published Aug. 16, 2012 and entitled Lockable Quick Coupling, the entire contents of which are incorporated herein by reference.

The pump graft 110 has a first end 112 that attaches to the second end 103 of the interposition graft 101 using any suitable attachment technique. As shown, the interposition graft 101 and pump graft 110 each include a sewing ring 105 and 115 (respectively). These rings can be sewn together to attach the interposition and pump grafts 101 and 110.

The pump graft 110 has a second end 113 that attaches to the CPD 10 (not shown) using any suitable connector (not shown).

An interior passage 114 (e.g. a tubular passage) is formed in the pump graft 110 that provides fluid communication with the CPD 10. Accordingly, when fully assembled, the graft 100 provides fluid communication from the vessel 300 through the interposition graft 101 and the pump graft 110 to the CPD 10.

In some embodiments, the graft 100 is configured to promote biological tissue growth on and around the interposition graft 101 (e.g., to improve connection to the vessel 100), while inhibiting tissue growth onto the pump graft 110 (e.g., to avoid interference with the operation of the CPD).

In some embodiments, this arrangement is advantageous for use with the CPD 10, e.g., in cases where blood flow both enters and exits the CPD 10 through the connection via graft 100 with vessel 300. Embodiments of the graft 100 described herein may advantageously provide hemocompatibility for flow in both directions, by promoting good washing through the graft and preventing or reducing thrombus formation.

This arrangement is in contrast to other blood pump devices such as ventricular assist devices (VADs). Typically, VADs have separate inflow and outflow conduits, and so do not require a graft connection of the type described herein.

In some embodiments, the interior passage 104 (and/or other surfaces) of the interposition graft 101 includes a rough surface configured to promote biological growth on the surface. In some embodiments, the rough surface includes a fabric material. In some embodiments, the fabric material includes a fabric including polymer fibers. In some embodiments, the fibers include polyester fibers. For example, in some embodiments, the interposition graft 101 may be constructed from a length of DACRON® fabric familiar to those skilled in the art.

In some embodiments, the interior passage 114 of the pump graft 110 includes a smooth or substantially smooth surface configured to inhibit biological growth on the surface. For example in some embodiments, the pump graft 110 may be made of a plastic or other suitable material, e.g., a molded and/or expanded thermoplastic polymer. In some embodiments, the polymer includes a fluoropolymer, e.g., polytetrafluoroethylene (PTFE). In some embodiments, the interior passage 114 of the pump graft 110 may be coated (e.g., using a silicone coating) to further enhance the smoothness of the passage.

In some embodiments, the physical shape of the interposition graft 101 and/or the pump graft 110 may be designed to prevent tissue ingrowth into the interior passage 114 of the pump graft 110. For example, as shown the interposition graft 101 is shaped to prevent contact between the rough surface or surfaces of the interposition graft 101 and the smooth surface of the interior passage 114 of the pump graft 110. The interior passage 104 of the interposition graft 101 has a so called "chimney feature" 106, a region of increased diameter located proximal to the connection with the pump graft 110. The chimney feature 106 is positioned such that the first end 112 of the pump graft 110 extends into the interior passage 104 of the interposition graft 101 without making physical contact with any rough surface. In some embodiments this may inhibit or substantially prevent tissue ingrowth into the inner passage 114 of the pump graft 110.

In typical cases, the surgical access to the vessel 110 (e.g., the subclavian artery) may be limited and the visibility is restricted. To compensate for this, in some embodiments, the interposition graft 101 is made of a flexible material to allow it to be deformed. This allows the surgeon to see the cut edges of the artery while performing anastomosis of the interposition graft 101. After the anastomosis of the interposition graft 110 is complete, the pump graft 110 is attached to the interposition graft, e.g. using the sewing 105 and 115 or any other suitable technique. In some embodiments the elasticity of the interposition graft 101 sufficient to keep the interface between vessel and graft open i.e. during the filling period of the pump.

In some embodiments, the length of the interposition graft 101 along the dimension from end 102 to end 103 may be shorter than the length of the pump graft 110 along the dimension from end 112 to end 113. For example, in some embodiments the length of the pump graft 110 may be at least 1.25, 1.5, 1.75, 2.0, 2.5, 3.0, 3.5, 4.0, 4.5, 5.0, 5.5, 6.0 or more times the length of the interposition graft.

Figure 4:
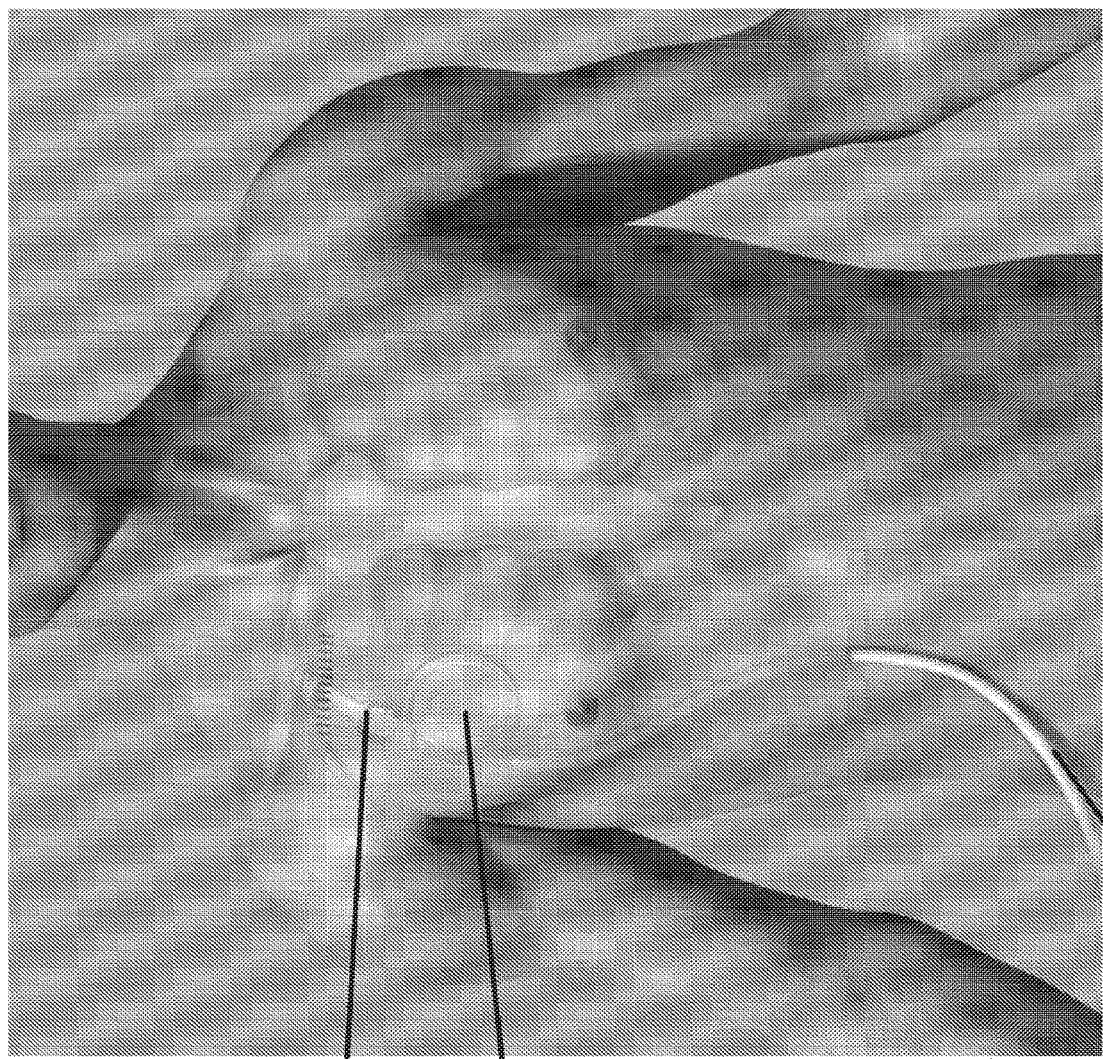
FIG. 4 illustrates the implantation of a CPD device in a human subject.

FIG. 4 shows an illustration of the CPD 10 implanted in a human subject. In some embodiments, the CPD maybe implanted using techniques described in the references incorporated above, or any other suitable techniques.

Figure 5:
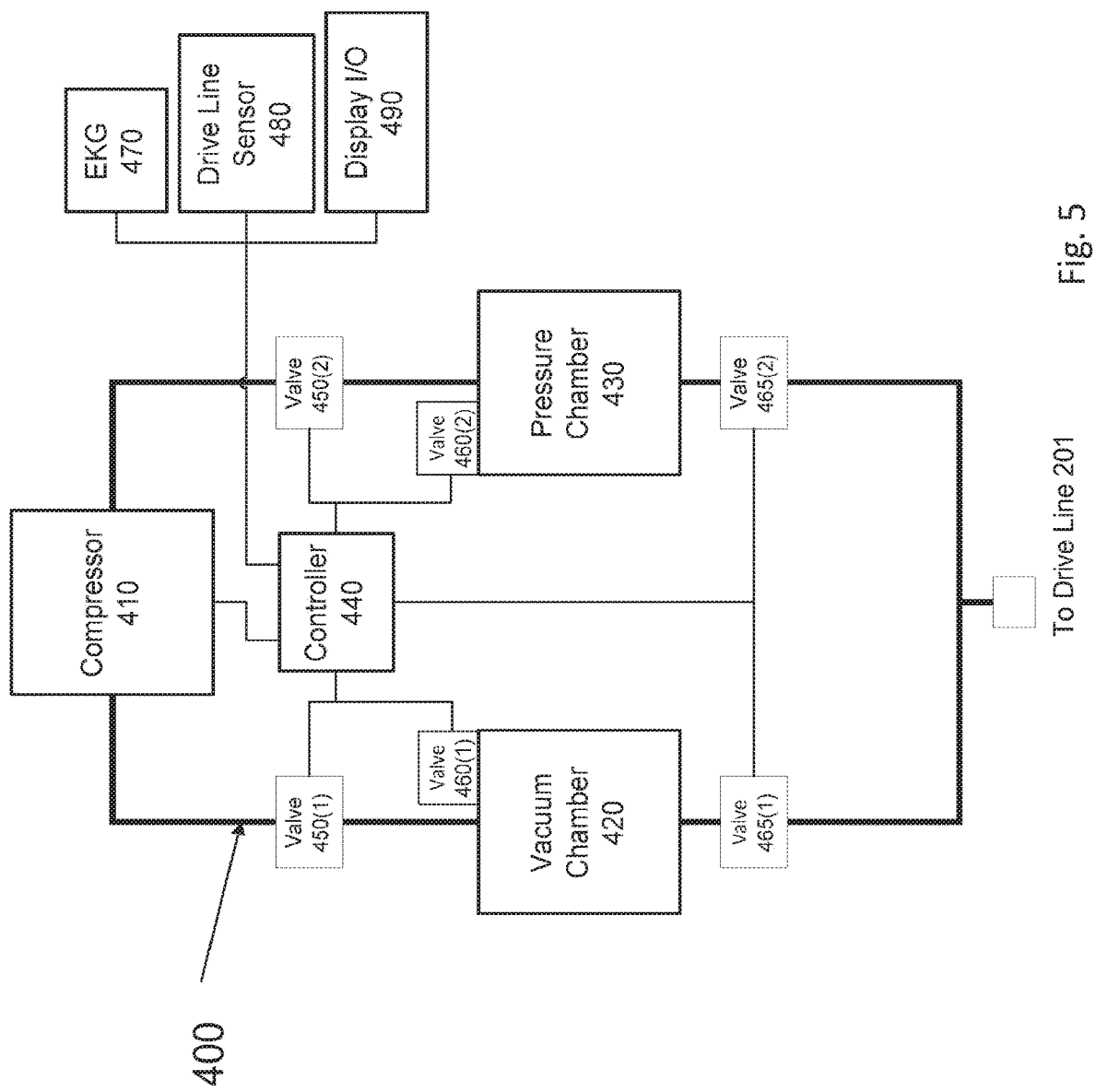
FIG. 5 is a functional block diagram illustration of a CPD drive controller.

FIG. 5 shows an exemplary embodiment of the CPD drive controller 202 in greater detail. As described below, a controller 440 (e.g., comprising one or more processors) implements a control loop to control the CPD 10 to provide advantageous performance, e.g., to ensure proper timing of the filling and emptying of the CPD 10 during each pumping cycle (corresponding to a heart beat). In some embodiments, the controller 440 receives feed back from an electrocardiogram (EKG) 470 and drive line sensor 480. In various embodiments, the drive line sensor 480 may be any suitable sensor capable of detecting the pressure within the drive line.

The controller 440 drives the CPD 10 by controlling the operation of a pump unit 400, e.g. by interfacing with a number of drive line valves 465, venting valves 460, chamber filling valves 450, and a compressor 410. Additionally, in some embodiments, the controller 440 may interface with a display and or input/output (I/O) device via a display I/O unit 490 to, e.g., to report subject and system status to a user and/or control operation of the CPD 10.

In various embodiments, one or more of the components of system 200, including the drive controller 202 may be of the Symphony® line of products available from Abiomed, Inc. of Danvers, Mass.

As set forth above, the drive controller 202 includes a vacuum chamber 420 and a pressure chamber 430. In some embodiments, the pulsatile positive pressure and vacuum supplied to the drive line 201 cause the CPD 10 to empty and fill, respectively. The controller 440 may control the opening and closing of valve 450(1) and valve 450(2) to positively pressurize the pressure chamber 430 and negatively pressurize the vacuum chamber 420. In some embodiments, one or both of the valves 450 may be omitted.

In some embodiments, the compressor 410 may push gas from the vacuum chamber side of the loop to the pressure chamber side of the loop to induce the respective negative and positive pressures. In other embodiments, the compressor may pump gas in from the external environment or a gas supply line to pressurize the pressure chamber 430. Similarly, the compressor 410 may pump gas from the vacuum chamber into the external environment to induce a vacuum in the vacuum chamber 420. In some embodiments, multiple compressors may be used, e.g., a first compressor attached to the vacuum chamber and a second compressor attached to the vacuum chamber 420 and pressure chamber 430.

In some embodiments, the chamber venting valves 460(1) and 460(2) of the vacuum chamber 420 and pressure chamber 430, respectively, allow the controller 440 to adjust the pressure of the vacuum chamber 420 and pressure chamber 430. For example, if the controller 440 determines the pressure in the pressure chamber 430 is too high, the control controller may execute a controlled release of the pressure from the system by opening the pressure chamber venting valve 460(2). Additionally or alternatively, the pressure within the vacuum chamber 420 and pressure chamber 430 may be controlled by controlling the speed or other operating parameter of the compressor 410.

In some embodiments, the pulsatile filling and emptying of the CPD 10 is generated by alternatively pressurizing and depressurizing the drive line. In some embodiments, the controller 440 drives the filling and emptying of the CPD 10 by alternatively activating the drive line valves 465(1) and 465(2). For example, by opening the drive line valve 465(1) and exposing the drive line to the negative pressure of the vacuum chamber 420, a negative pressure is induced in the drive line. The resulting negatively pressurized drive line causes the CPD 10 to fill with blood from the subject. After the drive line valve 465(1) closes, the controller may open the drive line valve 465(2) to induce a positive pressure in the drive line. The induced positive pressure in the CPD 10 causes the CPD 10 to empty of blood. In some embodiments, once one of the respective drive line valves 465 close, the controller 440 opens the respective filling valve 460 and activates the compressor 410 to repressurize the respective chamber to the appropriate pressure level. In some embodiments, the positive and negative pressures described above and below are gauge pressures relative to atmospheric pressure. In other embodiments, the pressures described are gauge pressures relative to the subject's blood pressure.

As described herein, the drive controller 202 may regulate the pulsatile actions of the system based on subject physiological and system recordings. As described above, the controller 440 may receive a subject's EKG as an input. In some embodiments, the controller 440 synchronizes the opening of the drive line valves with the contractions of a subject's heart. For example, controller may analyze the EKG and synchronize the external pumping of blood from the CPD 10 with the subject's heart's cycle to assist the circulation and decrease the work of the heart. The controller may cause the CPD 10 to eject blood (e.g., by applying positive pressure to the drive line) when the heart is relaxing to increase blood flow and oxygen to the heart, and to fill the pump passively or actively (e.g., by applying reduced pressure, for example negative pressure or vacuum to the drive line) when the heart is contracting to eject blood to decrease the heart's workload and lessen oxygen demand. For example, in some embodiments, responsive to the EKG signal, the controller 440 may alternatively open the drive line valve 465(2) to positively pressurize the drive line and empty the CPD 10, and open the drive line valve 465(1) to apply vacuum to the drive line to fill the CPD 10. Accordingly, the pumping action of the CPD 10 may be synched to the subject's heartbeat to provide counterpulsation. Responsive to detecting a contraction of the heart, the controller 440 may open the drive line valve 465(2) to positively pressurize the drive line and empty the CPD 10. In other embodiments, the controller 440 may additionally, or alternatively, include readings from a sphygmomanometer or any other sensor capable of detecting the subject's heart beat to drive the emptying and filling of the CPD 10.

Figure 6:
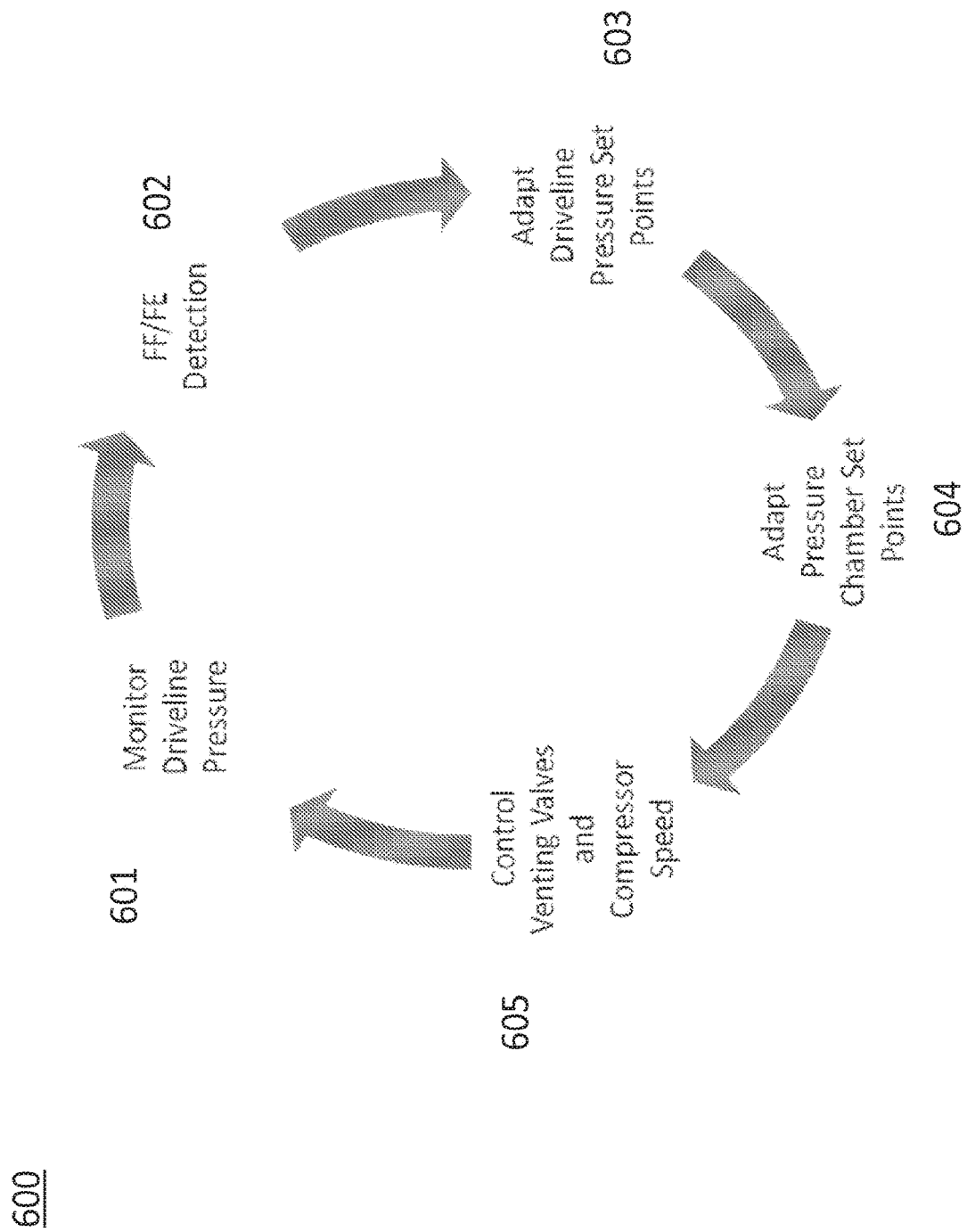
FIG. 6 is a flow diagram for a method of controlling a CPD drive controller.

FIG. 6 illustrates an exemplary control loop 600 that may be used by the CPD drive controller 202. In step 601, the pressure of the drive line 201 is monitored, using any suitable sensor. In step 602, the drive line pressure is analyzed (e.g., using any of the techniques described below) to determine information indicative of the operation of the CPD 10. For example, as shown, the drive line pressure is analyzed to determine when a full fill (FF) and full empty (FE) condition occur during each pumping cycle of the CPD. In steps 603, the operation of the CPD drive controller 202 is adjusted based on the information determined in step 602. For example, as shown, in step 603 drive line pressure set points are adjusted based on the drive line pressure information in order to adjust the timing of the FF and FE of CPD 10. In steps 604 and 605, the new drive line set points are implemented by adjusting various operating characteristics of the drive controller 202. For example, as shown, in step 604, the pressure set points for chambers 420 and 430 are adjusted, and in step 605, the operation of the valves 460(1) and 460(2) and/or the speed or other operating parameter of the compressor 410 are adjusted to implement the set points.

In the following exemplary embodiments of each of the steps in the control loop 600 are described in detail.

Detection of FF/FE

Figure 7:
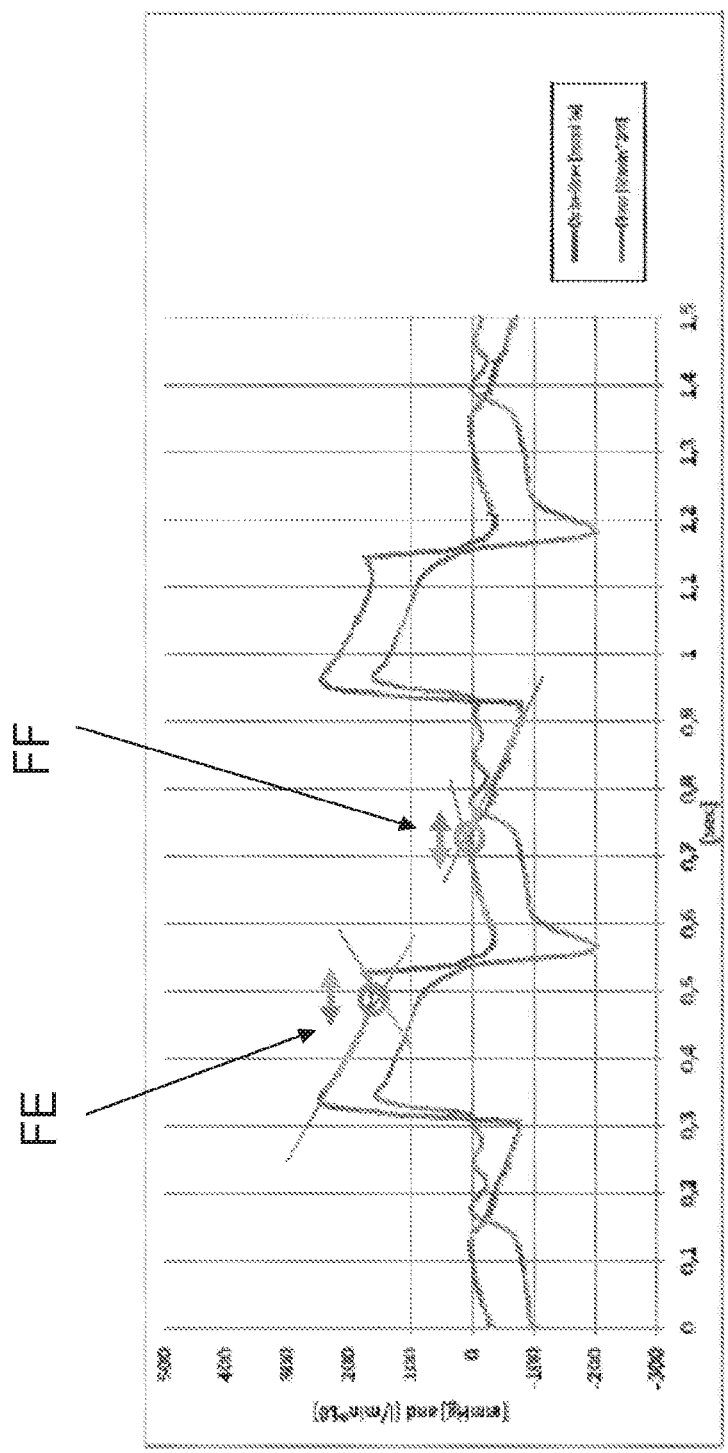
FIG. 7 illustrates detection of the full fill and full empty condition of a CPD using a drive line pressure signal.

In some embodiments, the full fill (FF) and the full empty (FE) condition of the CPD 10 are detected by monitoring the drive line pressure. In some embodiments, in the FF and FE states a membrane separating the drive chamber and the blood chamber of the CPD 10 reaches an end position (e.g., a stationary position which will not change with further increase of the absolute valve of the applied drive line pressure), which results in a significant pressure change. For example, FIG. 7 shows a plot of drive line pressure and measured blood flow as a function of time. The plot shows a drive line pressure and measured blood flow as a function of time. The plot shows drive line pressure in mmHg versus time and flow (l/min*10) versus time. At time zero the upper plot trace is the drive line pressure, while the lower plot trace is the flow. As shown, the FF and FE conditions are indicated by a kink in the pressure graph. In some embodiments, the drive line pressure signal is analyzed using an algorithm that detects these pressure changes by determining the slope of the pressure signal. For example, as shown, the FF and FE conditions are detected as a sudden change in the slope of the pressure signal.

The FE condition may be detected as positive slope in the drive line pressure signal during emptying with a blanking period after start of emptying. The FF condition may be detected as negative slope in the drive line pressure signal during the filling period with a blanking after start of filling.

In some embodiments, the time period for reaching FF and FE from the start of filling/emptying respectively may be the basis for setting the drive line pressure setpoints as described below.

Adjustment of Driveline Pressure

Emptying Cycle

Figure 8:
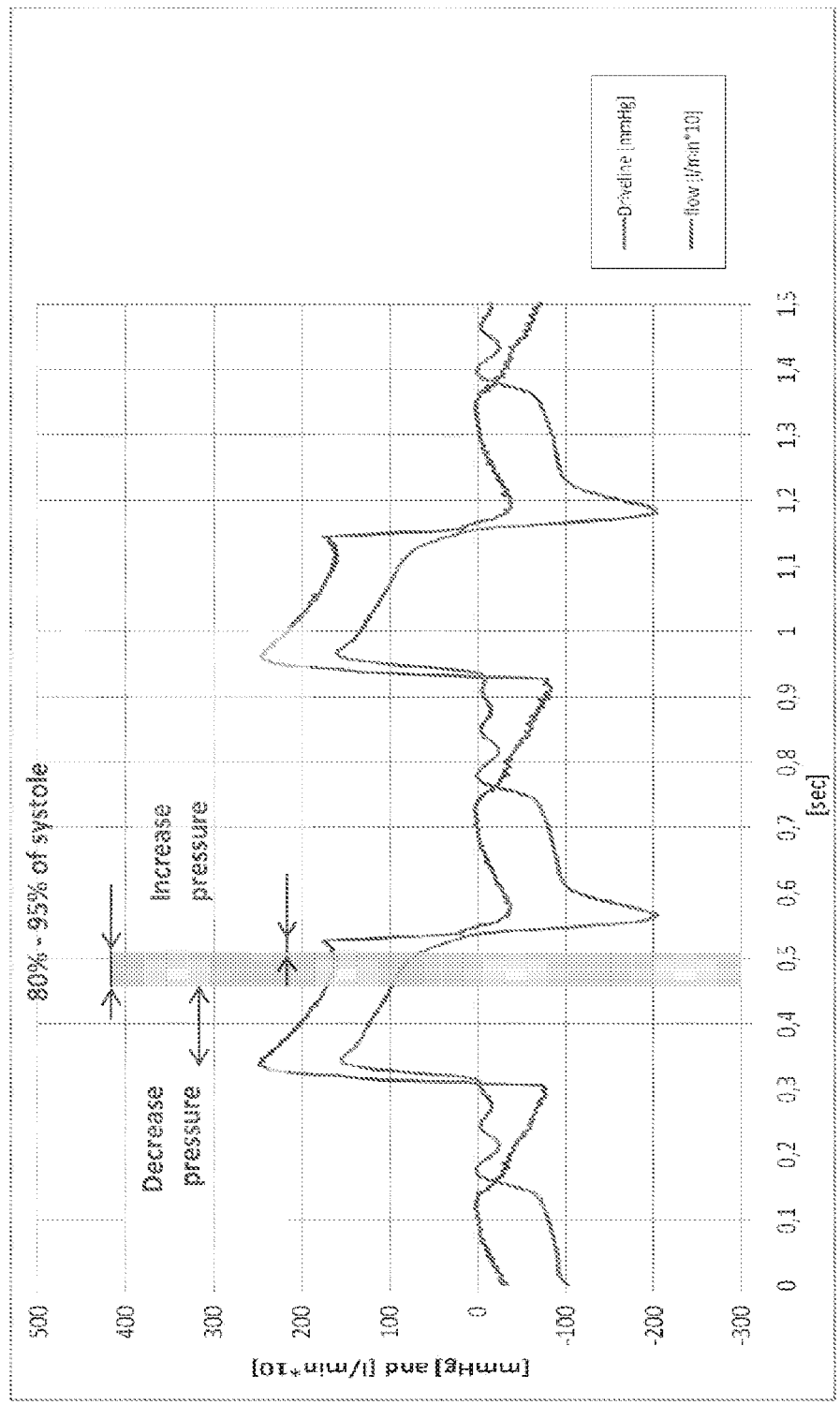
FIG. 8 illustrates a technique for adjustment of full empty occurrence for a CPD using a drive line pressure signal.

Referring to FIG. 8, the start of emptying of the CPD 10 may be determined by detecting the rising edge of the driveline pressure. During emptying an algorithm may be used that traces the full-empty occurrence (e.g., based on the pressure curve characteristic as described above) and calculates the relative or absolute time when it occurs. As shown, the relative time is determined as a percentage of the full emptying duration. In some embodiments, the drive controller 202 adjusts the drive line pressure to maintain the temporal location of the FE occurrence within a desired range (referred to herein as a "hysteresis"). As shown, the range is 80%-95% of the total emptying duration, however, in other embodiments other ranges may be used. If a FE condition time is detected exceeding the range (or when no FE condition is detected at all during the emptying duration), the drive line pressure is increased to allow for faster emptying. If the FE condition time is below the desired range, the drive line pressure is decreased to slow down the emptying.

Filling Cycle

The start of filling is assessed by detecting the falling edge in the driveline pressure. During the filling duration, the occurrence of the FF condition is detected (e.g., based on the pressure curve characteristics as described above) and then the relative or absolute fill time maybe determined. As shown the absolute fill time is determined. The absolute fill time may then be compared with a desired range (e.g., as shown the range is 150 ms-300 ms, although in other embodiments other ranges may be used). The drive controller 202 may adjust the drive line pressure to ensure the absolute fill time is kept within the desired range. For example, in some embodiments, the absolute value of the negative pressure during the fill duration may be increased to speed filling or decreased to slow filling.

In some embodiments, the range of setpoints for pressure and vacuum in the driveline are limited, e.g., in the software of the controller 440, e.g. for patient security reasons.

Adjustment of Pump Unit Operating Parameters

As described above, in various embodiments, the controller 202 may adjust the pressure supplied to the drive line 201 by controlling the operation of the pump unit 400 in pneumatic communication with the drive line 201.

For example, in some embodiments, during the filling of the CPD 10, the driveline is coupled to a vacuum chamber 420, while during emptying the CPD 10 is coupled to a pressure chamber 430. In some embodiments, the desired drive line pressure set points during filling and emptying may be controlled indirectly by controlling the pressure set points for the chambers 420 and 430.

Figure 9:
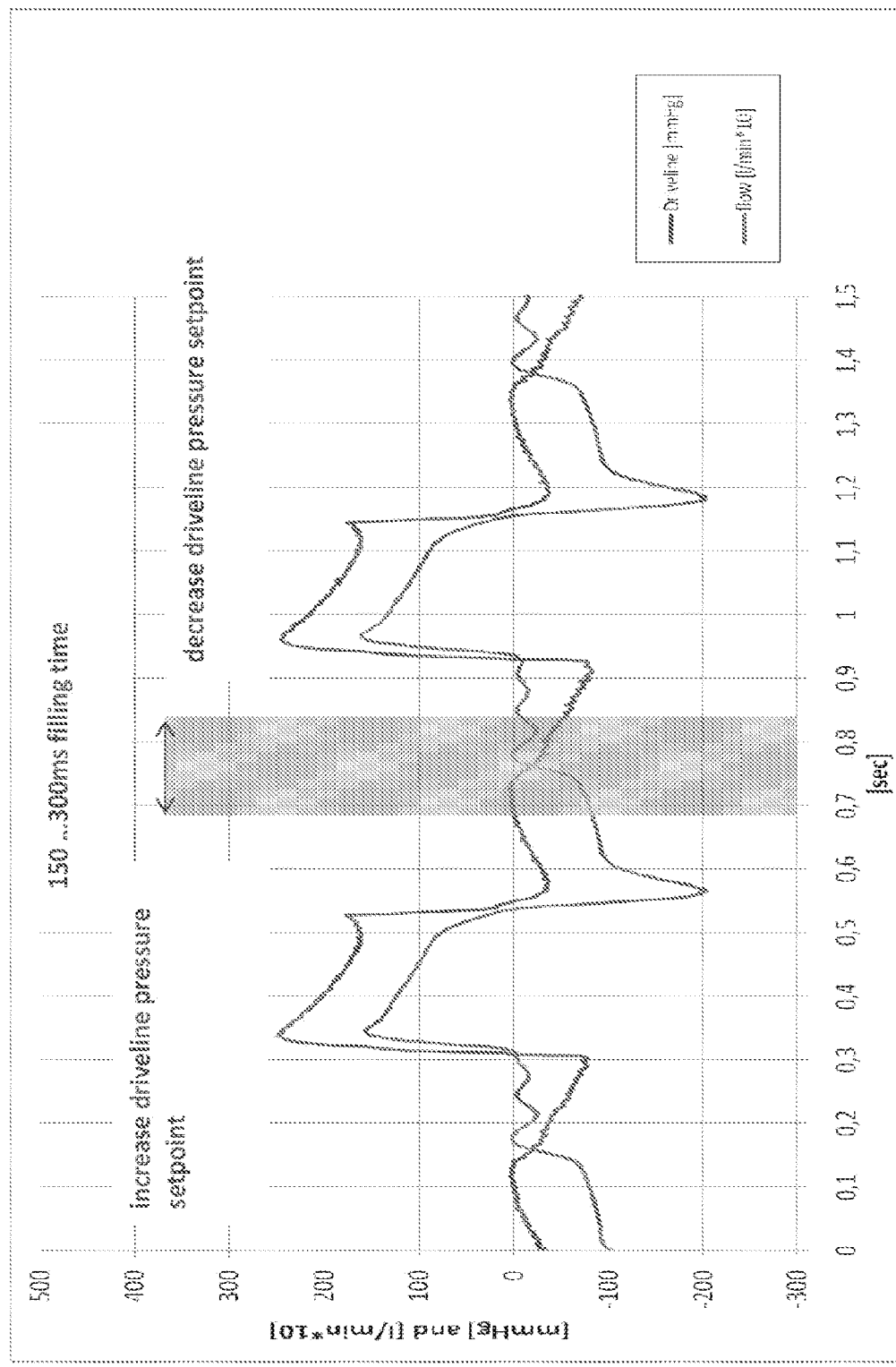
FIG. 9 illustrates a technique for adjustment of full fill occurrence for a CPD using a drive line pressure signal.
Figure 10:
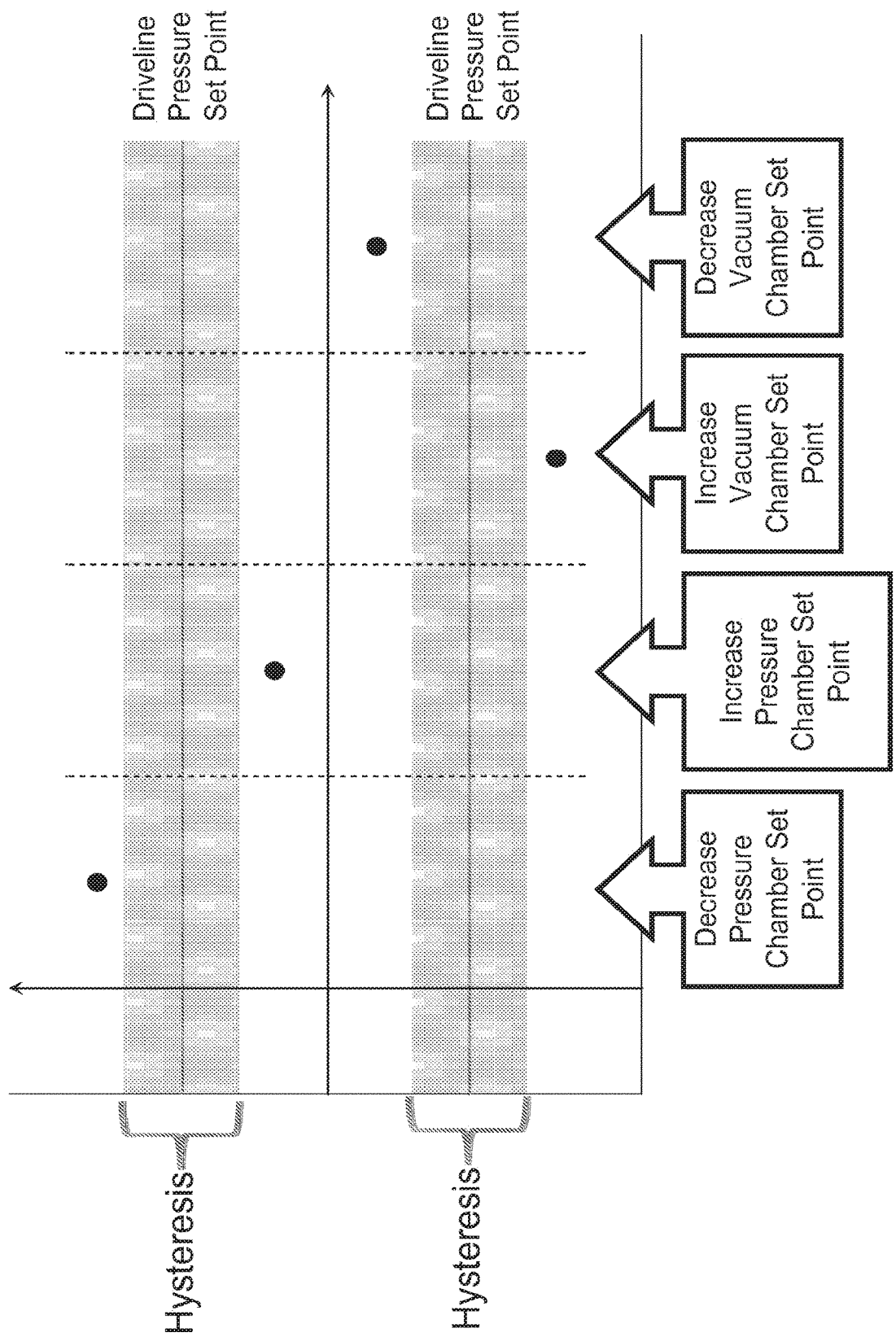
FIG. 10 illustrates an exemplary embodiment of a control scheme for adjusting CPD drive line pressure.
Figure 11:
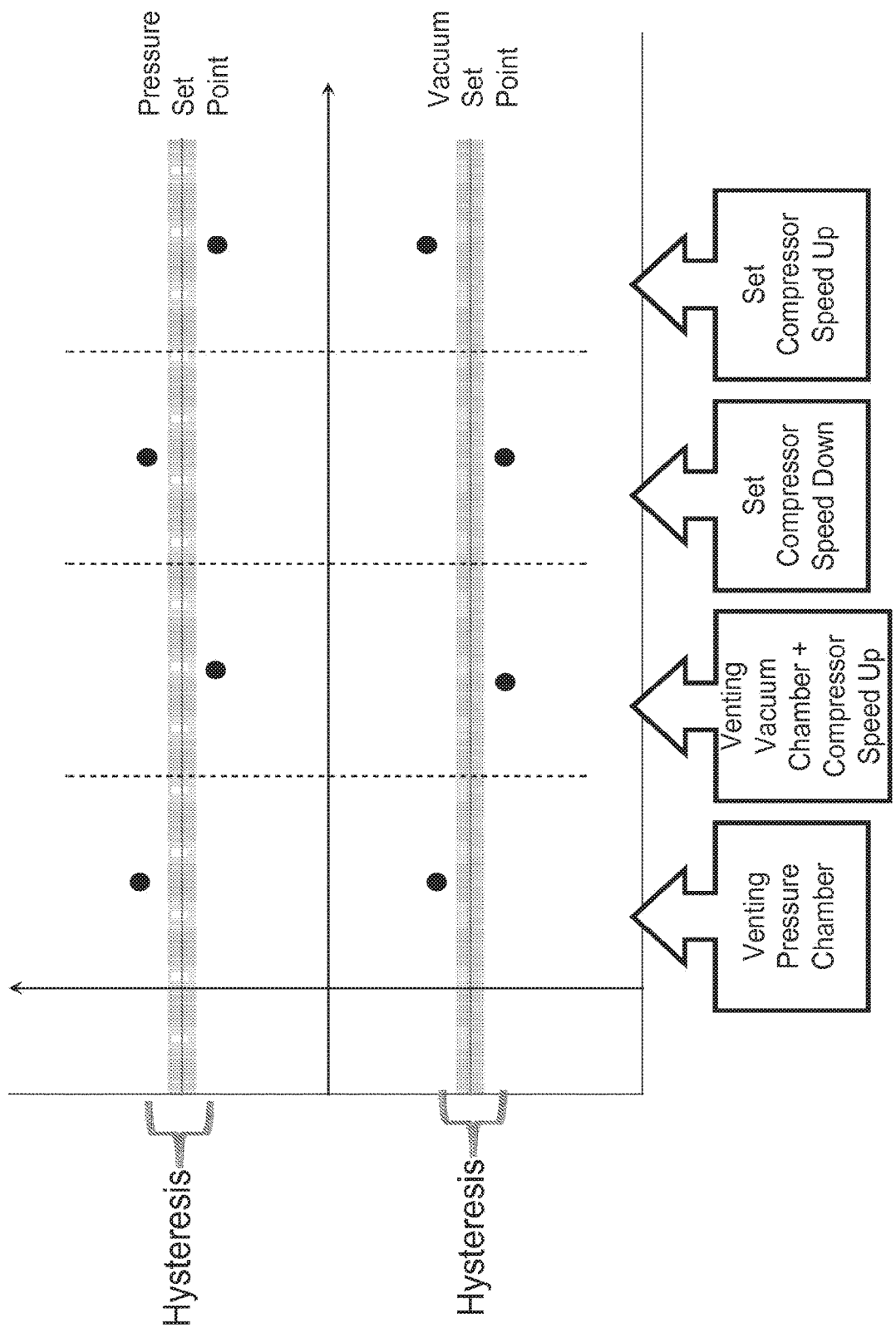
FIG. 11 illustrates an exemplary embodiment of a control scheme for the operation of a CPD pump unit by a controller.

This indirect control is illustrated in FIGS. 10 and 11. FIG. 9 illustrates control of driveline pressure via plenum pressure. The four labeled driver reactions, running from left to right along the x-axis are Decrease Pressure Chamber Set Point, Increase Pressure Chamber Set Point, Increase Vacuum Chamber Set Point, and Decrease Vacuum Chamber Set Point. The y-axis shows measured pressure values in arbitrary units. During emptying, the action Decrease Pressure Chamber Set Point occurs when the measured driveline pressure is greater than the desired range for the drive line pressure set point. The action Increase Pressure Chamber Set Point occurs when the measured drive line pressure is less than the desired range for the drive line pressure set point.

Similarly, during filling, the action Increase Vacuum Chamber Pressure occurs when the driveline pressure is less than the desired range for the drive line pressure. The action Decrease Vacuum Chamber Pressure occurs when the driveline pressure is greater than the desired range for the drive line pressure.

In some embodiments, vacuum and pressure chambers 420 and 430 are fed by the same compressor 410, and the controller 440 may be used to regulate compressor speed and/or venting valves 460(1) and 460(2) to perform adjustments for pressure and vacuum synchronously.

In some embodiments, the compressor speed defines the total pressure difference between pressure in between the vacuum chamber 420 and the pressure chamber 430. By that increasing the compressor speed one may increase pressure and lower vacuum simultaneously. Of course in other embodiments, more than one compressor may be used to allow independent control of the pressure and vacuum chambers.

In some embodiments, control of the venting valves 460(1) and 460(2) allow for raising and lowering the overall system pressure. If the pressure chamber 430 is vented, the amount of air in the closed loop pneumatic system is reduced resulting in lower absolute values for pressure and vacuum. If the vacuum chamber 420 is vented the amount of air in the pneumatic systems is increased resulting in higher absolute values for pressure and vacuum. In some embodiments, the vacuum chamber venting valve only opens during the emptying phase so as not to interfere with the filling period. In some embodiments, the pressure chamber venting valve only opens during the filling phase to not interfere with the emptying period.

FIG. 11 illustrates one exemplary embodiment of a control scheme for the operation of the pump unit 400 by the controller 440. The x-axis shows driver actions. The y-axis shows corresponding measured pressure values in arbitrary units. Moving from left to right, if the measured drive line pressure is above a desired range for both filling and emptying, the pressure chamber 430 is vented. If the measured drive line pressure is below a desired range for both filling and emptying, the vacuum chamber 420 is vented, and the speed of compressor 410 increased. If the measured drive line pressure is too high during emptying, but too low during filling, the speed of compressor 410 is decreased without any venting. If the measured drive line pressure is too low during emptying, but too high during filling, the speed of compressor 410 is increased without any venting.

In some embodiments, the range of setpoints for the pressure chamber 430 and may be limited, e.g., mechanically or by software used by the controller 440. In some embodiments, in the case that the pressure in the chamber 430 exceeds the upper limit the corresponding venting opens, e.g., for a defined timeframe or until an acceptable pressure is detected.

In some embodiments, the range of setpoints for the vacuum chamber 420 may be limited e.g., mechanically or by software used by the controller 440. In some embodiments, in the case that the pressure in the chamber 420 is below a lower limit, the corresponding venting valve opens, e.g., for a defined timeframe or until an acceptable pressure is detected.

Although the devices and techniques described herein have been described for used with a CPD, it is to be understood that in various embodiments they may be applied to other types of blood pumps.

It is to be understood that as used herein, the term vacuum is not to be understood to refer to the complete absence of matter within a volume, but rather to pressures less than the ambient pressure of a given system.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screen for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprises any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods of processes outlined herein may be coded as software that is executable on one or mere processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor device, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed, by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or" as used herein in the specification and in the claims, should be understood to mean "either or both" of the elements so conjoined, i.e., elements that are conjunctively present in some cases and distinctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all translational phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An apparatus for controlling operation of a counterpulsation device (CPD) in a human or animal subject, the apparatus comprising a controller configured to:
provide counterpulsation therapy by controlling pressure supplied to a CPD drive line;
while providing counterpulsation therapy, receive a CPD drive line pressure signal indicative of the pressure in the CPD drive line; and
adjust the pressure supplied to the drive line based at least in part on the drive line pressure signal, by performing at least one of: exposing the drive line to a negative pressure of a vacuum chamber to fill a CPD chamber as a heart is contracting and exposing the driveline to a positive pressure of a pressure chamber to empty the CPD chamber as the heart is relaxing.

2. The apparatus of claim 1, wherein the CPD drive line is in pneumatic communication with the CPD.

3. The apparatus of claim 1, wherein the controller is further configured to receive a pressure upper limit corresponding to an upper limit of the pressure in the CPD drive line and a pressure lower limit corresponding to a lower limit of the pressure in the CPD drive line, wherein the controller adjusts the pressure supplied to the CPD drive line by:
in response to determining that the pressure in the CPD drive line exceeds the pressure upper limit, venting the pressure chamber until the pressure in the CPD drive line is below the pressure upper limit, and
in response to determining that the pressure in the CPD drive line is below the pressure lower limit, opening a valve corresponding to the vacuum chamber until the pressure in the CPD drive line is above the pressure lower limit.

4. The apparatus of claim 3, wherein venting the pressure chamber induces a negative pressure in the drive line, causing the CPD to fill with blood from the subject, and opening the valve corresponding to the vacuum chamber induces a positive pressure in the CPD drive line, causing the CPD to empty of blood.

5. The apparatus of claim 1, wherein the controller is configured to adjust the pressure supplied to the CPD drive line based at least in part on the CDP drive line pressure signal by analyzing the CPD drive line pressure signal to determine a full or an empty condition of the CPD by analyzing change in drive line pressure as a function of time.

6. The apparatus of claim 5, wherein:
the CPD comprises a drive chamber in pneumatic communication with the drive line and a blood chamber that is sealed from the drive chamber by a membrane, and
the controller analyzes the CPD drive line pressure signal to determine the full or the empty condition of the CPD by detecting a feature in the drive line pressure signal indicative of the membrane reaching a substantially stationary end position.

7. The apparatus of claim 5, wherein the controller is further configured to:
detect a temporal location of the full or the empty condition during an operational cycle of the CPD;
compare the temporal location to a desired range; and
if the temporal location is outside of the desired range, adjust the pressure supplied to the CPD drive line.

8. The apparatus of claim 7, wherein the controller is further configured to, during emptying of the CPD:
determine if the temporal location of the empty condition occurs at a time earlier than the desired range and, if so, adjust the drive line pressure to slow the emptying; and
determine if the temporal location of the empty condition occurs at a time later than the desired range or does not occur and, if so, adjust the drive line pressure to speed up the emptying.

9. The apparatus of claim 7, wherein the controller is further configured to, during filling of the CPD:
determine if the temporal location of the full condition occurs at a time earlier than the desired range and, if so, adjust the drive line pressure to slow the filling;
and determine if the temporal location of the full condition occurs at a time later than the desired range or does not occur and, if so, adjust the drive line pressure to speed up the filling.

10. The apparatus of claim 1, wherein the controller is configured to adjust the pressure supplied to the drive line by adjusting one or more operating parameters of a pump device pneumatically coupled to the CPD drive line.

11. A method for controlling operation of a counterpulsation device (CPD) in a human or animal subject, the method comprising:
providing counterpulsation therapy by controlling pressure supplied to a CPD drive line;
while providing counterpulsation therapy, receiving a CPD drive line pressure signal indicative of the pressure in the CPD drive line; and
adjusting the pressure supplied to the drive line based at least in part on the drive line pressure signal, by performing at least one of: exposing the drive line to a negative pressure of a vacuum chamber to fill a CPD chamber as a heart is contracting and exposing the driveline to a positive pressure of a pressure chamber to empty the CPD chamber as the heart is relaxing.

12. The method of claim 11, wherein the CPD drive line is in pneumatic communication with the CPD.

13. The method of claim 12, further comprising receiving a pressure upper limit corresponding to an upper limit of the pressure in the CPD drive line and a pressure lower limit corresponding to a lower limit of the pressure in the CPD drive line, wherein adjusting the pressure supplied to the CPD drive line comprises:
in response to determining that the pressure in the CPD drive line exceeds the pressure upper limit, venting the pressure chamber until the pressure in the CPD drive line is below the pressure upper limit, and
in response to determining that the pressure in the CPD drive line is below the pressure lower limit, opening a valve corresponding to the vacuum chamber until the pressure in the CPD drive line is above the pressure lower limit.

14. The method of claim 13, wherein venting the pressure chamber induces a negative pressure in the drive line, causing the CPD to fill with blood from the subject, and wherein opening the valve corresponding to the vacuum chamber induces a positive pressure in the CPD drive line, causing the CPD to empty of blood.

15. The method of claim 11, wherein adjusting, based at least in part on the CDP drive line pressure signal, the pressure supplied to the CPD drive line by analyzing the CPD drive line pressure signal to determine a full or an empty condition of the CPD by analyzing change in drive line pressure as a function of time.

16. The method of claim 15, wherein:
the CPD comprises a drive chamber in pneumatic communication with the drive line and a blood chamber that is sealed from the drive chamber by a membrane, and
and wherein analyzing the CPD drive line pressure signal to determine the full or the empty condition of the CPD comprises detecting a feature in the drive line pressure signal indicative of the membrane reaching a substantially stationary end position.

17. The method of claim 15, further comprising:
detecting a temporal location of the full or the empty condition during an operational cycle of the CPD;
comparing the temporal location to a desired range; and
if the temporal location is outside of the desired range, adjusting the pressure supplied to the CPD drive line.

18. The method of claim 17, further comprising, during emptying of the CPD:

determining if the temporal location of the empty condition occurs at a time earlier than the desired range and, if so, adjusting the drive line pressure to slow the emptying; and determining if the temporal location of the empty condition occurs at a time later than the desired range or does not occur and, if so, adjusting the drive line pressure to speed up the emptying.

19. The method of claim 17, further comprising, during filling of the CPD:

determining if the temporal location of the full condition occurs at a time earlier than the desired range and, if so, adjusting the drive line pressure to slow the filling;

and determining if the temporal location of the full condition occurs at a time later than the desired range or does not occur and, if so, adjusting the drive line pressure to speed up the filling.

20. The method of claim 11, wherein adjusting the pressure supplied to the drive line comprises adjusting one or more operating parameters of a pump device pneumatically coupled to the CPD drive line.

\* \* \* \* \*

UNITED STATES PATENT AND TRADEMARK OFFICE
CERTIFICATE OF CORRECTION

PATENT NO. : 10,549,020 B2
APPLICATION NO. : 15/923734
DATED : February 4, 2020
INVENTOR(S) : Paul Spence et al.

Page 1 of 2

It is certified that error appears in the above-identified patent and that said Letters Patent is hereby corrected as shown below:

On the Title Page

Column 1, (71) Applicant, Delete "Drive," and insert --Danvers,--

In the Specification

Column 1, Background, Line 34, Delete "maybe" and insert --may be--

Column 2, Summary, Line 3, After "drive", insert --line--

Column 4, Detailed Description, Line 55, Delete "described" and insert --detailed--

Column 4, Detailed Description, Line 59, Delete "be" and insert --by--

Column 4, Detailed Description, Line 60, Delete "chambers" and insert --chamber--

Column 5, Detailed Description, Line 58, Delete "100)," and insert --300),--

Column 6, Detailed Description, Line 42, Delete "110" and insert --300--

Column 6, Detailed Description, Line 49, Delete "110" and insert --101--

Column 6, Detailed Description, Line 63, Delete "maybe" and insert --may be--

Column 9, Detailed Description, Line 60, Delete "maybe" and insert --may be--

Signed and Sealed this
Twenty-eighth Day of December, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,549,020 B2

In the Claims

Column 15, Line 30, In Claim 5, Delete "CDP" and insert --CPD--

Column 16, Line 46, In Claim 15, Delete "CDP" and insert --CPD--